US007148343B2

(12) United States Patent
Bair, Jr. et al.

(10) Patent No.: US 7,148,343 B2
(45) Date of Patent: *Dec. 12, 2006

(54) COMPOSITIONS AND METHODS FOR USING A SOLID SUPPORT TO PURIFY RNA

(75) Inventors: Robert Jackson Bair, Jr., Plymouth, MN (US); Ellen M. Heath, Livermore, CO (US); Heather Meehan, Ham Lake, MN (US); Kim Elayne Paulsen, Brooklyn Park, MN (US); John M. Wages, Jr., Tupelo, MS (US)

(73) Assignee: Gentra Systems, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/418,194

(22) Filed: Apr. 16, 2003

(65) Prior Publication Data

US 2004/0019196 A1 Jan. 29, 2004

Related U.S. Application Data

(63) Continuation-in-part of application No. 09/974,798, filed on Oct. 12, 2001.

(51) Int. Cl.
*C07H 21/02* (2006.01)
*C07H 21/04* (2006.01)

(52) U.S. Cl. ............... 536/25.4; 536/25.41; 536/25.42; 536/23.1; 536/22.1; 252/1; 435/6; 435/91.1; 435/91.3; 435/375; 435/193; 435/5

(58) Field of Classification Search .............. 536/25.4, 536/25.41, 25.42, 23.1, 22.1; 252/1; 435/6, 435/91.1, 91.3, 375, 193, 5
See application file for complete search history.

(56) References Cited

U.S. PATENT DOCUMENTS

| 4,483,920 | A | * | 11/1984 | Gillespie et al. ............... 435/6 |
| 4,843,155 | A | | 6/1989 | Chomczynski ............... 536/27 |
| 5,010,183 | A | | 4/1991 | Macfarlane ................... 536/27 |
| 5,057,426 | A | | 10/1991 | Henco ......................... 435/270 |
| 5,155,018 | A | | 10/1992 | Gillespie et al. .............. 435/91 |
| 5,234,809 | A | | 8/1993 | Boom et al. ................... 435/91 |
| 5,346,994 | A | | 9/1994 | Chomczynski ............. 530/419 |
| 5,405,951 | A | | 4/1995 | Woodard ................. 536/25.41 |
| 5,599,667 | A | | 2/1997 | Arnold et al. ................. 435/6 |
| 5,637,687 | A | * | 6/1997 | Wiggins .................... 536/25.4 |
| 5,728,822 | A | | 3/1998 | Macfarlane ............. 536/25.41 |
| 5,939,259 | A | * | 8/1999 | Harvey et al. ................. 435/6 |
| 5,945,515 | A | | 8/1999 | Chomczynski ............. 530/412 |
| 5,958,677 | A | | 9/1999 | Lee et al. ....................... 435/5 |
| 5,972,613 | A | | 10/1999 | Somack et al. ................ 435/6 |

(Continued)

FOREIGN PATENT DOCUMENTS

EP 0 818 461 1/1998

(Continued)

OTHER PUBLICATIONS

Macfarlane et al. "Isolating RNA from clinical samples with Catrimox-14 and lithium chloride." Abstract, J. of Clinical Lab. Anal., 11(3), 132-139 1997.*

(Continued)

*Primary Examiner*—Shaojia Anna Jiang
*Assistant Examiner*—Devesh Khare
(74) *Attorney, Agent, or Firm*—Viksnins Harris & Podys PLLP (57) ABSTRACT

Reagents, methods and kits for the purification of RNA from biological materials are provided.

20 Claims, 1 Drawing Sheet

U.S. PATENT DOCUMENTS

| | | | | |
|---|---|---|---|---|
| 5,973,137 | A | 10/1999 | Heath | 536/25.4 |
| 5,985,572 | A | 11/1999 | Macfarlane | 435/6 |
| 5,990,302 | A * | 11/1999 | Kuroita et al. | 536/25.4 |
| 6,037,465 | A | 3/2000 | Hillebrand et al. | |
| 6,204,375 | B1 | 3/2001 | Lader | 536/25.4 |
| 6,218,531 | B1 * | 4/2001 | Ekenberg | 536/25.41 |
| 6,465,639 | B1 * | 10/2002 | van Gemen et al. | 536/25.4 |
| 6,528,641 | B1 | 3/2003 | Lader | 536/25.4 |
| 6,699,987 | B1 * | 3/2004 | Hillebrand et al. | 536/25.4 |
| 2001/0041332 | A1 | 11/2001 | Hillebrand et al. | 435/6 |
| 2002/0001812 | A1 * | 1/2002 | Smith et al. | 435/6 |
| 2003/0073830 | A1 | 4/2003 | Heath et al. | |
| 2005/0032105 | A1 * | 2/2005 | Bair et al. | 435/6 |

FOREIGN PATENT DOCUMENTS

| | | |
|---|---|---|
| WO | WO-92/07863 | 5/1992 |
| WO | WO-95/01359 | 1/1995 |
| WO | WO-95/02049 | 1/1995 |
| WO | WO-95/34569 | 12/1995 |
| WO | WO 96/18731 * | 6/1996 |
| WO | WO-96/18731 | 6/1996 |
| WO | WO 03/33739 | 4/2003 |

OTHER PUBLICATIONS

Bugos et al., "RNA isolation from plant tissues recalcitrant to extraction in guanidine", BioTechniques, 19, 734-737 (1995).*

Chomczynski and Sacchi, "Single-step method of RNA isolation by acid guanidinium thiocyanate-phenol-chloroform extraction", Anal Biochem, 162, 156-159 (1987).*

Cox and Smulian, "A single-step procedure for the isolation of individual mRNA species from crude lysates of Physarum polycephalum", FEBS Letters, 155, 73-80 (1983).*

Krawetz et al., "Isolation and fractionation of total nucleic acids from tissues and cells", J Biochem Biophys Methods., 12, 29-36 (1986).*

Witchel et al., "Milligram quantity preparation of RNA from a marine invertebrate with a high fluid content", BioTechniques, 21, 1024-1026 (1996).*

CRC Handbook of Chemistry and Physics, 62nd Edition. CRC Press, Boca Raton, Florida, (1981-1982), D-96, B-75, B-91, B-113, B-132, B-147.

"Technical Bulletin # 160: The Use of LiCl Precipitation for RNA Purification", Ambion Website, http://www.abmbion.com/techlib/tb/tb_160.html, (2003), 5 pages.

Ahmad, Faizan, "Free Energy Changes in Denaturation of Ribonuclease A by Mixed Denaturants", The Journal of Biological Chemistry, 259 (7), (Apr. 1984), 4183-4186.

Ahmad, Faizan, "Free Energy Changes in Ribonuclease A Denaturation", The Journal of Biological Chemistry, 258 (18), (1983), 11143-11146.

Collins, Kim D., "Sticky ions in biological systems", Proceedings of the National Academy of Sciences USA, 92, (Jun. 1995), 5553-5557.

Kazakov, Sergei A., "Nucleic Acid Binding and Catalysis by Metal Ions", Bioorganic Chemistry: Nucleic Acids, Chapter 9, Oxford University Press, New York, (1996), 244-477.

Sambrook, Joseph, et al., "Concentrating Nucleic Acids: Precipitation with Ethanol or Isopropanol", Molecular Cloning: a Laboratory Manual, vol. 3, 2nd Edition, Cold Spring Harbor Laboratory Press, (1989), E10 & E15.

Wiggins, Philippa M., "High and Low Density Intracellular Water", Cellular and Molecular Biology, 47 (5), (2001), 735-744.

"Kosmotropes and Chaotropes," http://www.lsbu.ac.uk/water/kosmos.html printed Aug. 18, 2004.

Galinski et al., "The Kosmotropic (structure-forming) Effect of Compensatory Solutes," Comp. Biochem. Physiol., 1997, 117A(3):357-365.

Hofmeister, "On the Theory of the Effects of Salts," Arch. Exp. Pathol. Pharmakol., 1888, 24:247-260.

Lever et al., "Some Ways of Looking at Compensatory Kosmotropes and Different Water Environments," Comp. Biochem. Physiol., 2001, 130A:471-486.

Washabaugh and Collins, "The Systematic Characterization by Aqueous Column Chromatography of Solutes Which Affect Protein Stability," J. Biol. Chem., 1986, 261(27):12477-12485.

Dahle and Macfarlane, "Isolation of RNA from Cells in Culture Using Catrimox-14™ Cationic Surfactant," BioTechniques, 1993, 15(6):1102-1105.

* cited by examiner

Figure 1

COMPOSITIONS AND METHODS FOR USING A SOLID SUPPORT TO PURIFY RNA

CROSS-REFERENCE TO RELATED APPLICATIONS

This application is a continuation-in-part of U.S. application Ser. No. 09/974,798, filed Oct. 12, 2001, which is incorporated by reference herein.

BACKGROUND OF THE INVENTION

Nucleic acids such as deoxyribonucleic acid (DNA) and ribonucleic acid (RNA) are used extensively in the field of molecular biology for research and clinical analyses. RNA may be found in nature in various forms, including messenger RNA (mRNA), transfer RNA (tRNA), ribosomal RNA (rRNA), and viral RNA. Each of these types of RNA have distinct properties related to their specific functions. Analysis of RNA expression levels and patterns provides important information in fields such as developmental genetics, drug discovery and clinical diagnostics. For example, RNA analysis provides important diagnostic information about both normal and aberrant functioning of genes. Furthermore, gross DNA rearrangements associated with common leukemias are detected by isolation and identification of abnormal, hybrid RNAs.

Common methods for analyzing RNA include northern blotting, ribonuclease protection assays (RPAs), reverse transcriptase-polymerase chain reaction (RT-PCR), cDNA preparation for cloning, in vitro translation and microarray analyses. To obtain valid and consistent results from these analyses, it is important that the RNA be purified from other components common to biological materials such as proteins, carbohydrates, lipids and DNA.

RNA purification methods fall into two general categories, liquid phase and solid phase purification. In liquid phase purification, the RNA remains in the liquid phase while impurities are removed by processes such as precipitation and/or centrifugation. In solid phase purification, the RNA is bound to a solid support while impurities such as DNA, proteins, and phospholipids are selectively eluted. Both purification strategies utilize conventional methods, which require numerous steps and, often, hazardous reagents, as well as more rapid methods, which require fewer steps and usually less hazardous reagents. When the starting biological material comprises cells, both methods require a cell or viral co-rupture or lysis step that results in a mixed RNA with contaminants such as DNA, lipids, carbohydrates, proteins, etc. Such mixtures also contain RNases that easily degrade RNA and must be removed and/or inactivated.

Traditionally, liquid phase RNA isolation methods have used liquid-liquid extraction (i.e, phenol-chloroform) and alcohol precipitation. Perhaps the most commonly used liquid-liquid extraction method is the "acid-guanidinium-phenol" method of Chomczynski and Sacchi (Chomczynski P, Sacchi N., *Single-step method of RNA isolation by acid guanidinium thiocyanate-phenol-chloroform extraction*, Anal Biochem 162: 156–9 [1987]; U.S. Pat. Nos. 5,945,515, 5,346,994, and 4,843,155). This method comprises: (1) extracting the sample with a guanidinium isothiocyanate (GITC) solution to which an acidic medium, phenol, and chloroform are added consecutively; (2) centrifuging the mixture to separate the phases such that the proteins denatured by the phenol may be removed from the nucleic acids that are found in an intermediate layer; (3) adding an alcohol so as to precipitate and thereby concentrate the RNA; and (4) washing and re-hydrating the purified RNA. Although this method ensures the purification of RNA, it utilizes hazardous reagents such as chloroform and phenol. Precipitation of nucleic acids by cationic detergents is another example of liquid phase technology (U.S. Pat. Nos. 5,985,572; 5,728,822 and 5,010,183 (MacFarlane)). For example, U.S. Pat. No. 5,985,572 discloses a novel method for isolating RNA from biological samples using selected quaternary amine surfactants. A non-hazardous liquid phase purification method was disclosed by Heath (U.S. Pat. No. 5,973,137) using low pH lysing and precipitation reagents. However, liquid phase methods have serious disadvantages in that they involve tedious precipitation steps, and are consequently difficult to automate. Thus, the need for high-throughput RNA purification has led to the development of solid phase methods.

As with liquid phase purification, conventional solid phase methods have been developed to generate highly purified RNA. Generally, these methods require four general steps: lysing cells or viral coats to release RNA; binding the released RNA to a solid support; washing away impurities; and then eluting the purified RNA. The first two steps, lysing the cells or viral coats and binding the released RNA, have traditionally required hazardous reagents.

For solid phase nucleic acid isolation methods, many solid supports have been used including membrane filters, magnetic beads, metal oxides, and latex particles. Probably the most widely used solid supports are silica-based particles (see, e.g., U.S. Pat. No. 5,234,809 (Boom et al.); International Publication No. WO 95/01359 (Colpan et al.); U.S. Pat. No. 5,405,951 (Woodard); International Publication No. WO 95/02049 (Jones); WO 92/07863 (Qiagen GmbH). One method for binding nucleic acids to silica is by the use of chaotropic agents. For example, the method disclosed in U.S. Pat. No. 5,234,809 (Boom et al.) uses a high concentration chaotropic solution such as guanidine isothiocyanate to bind DNA to silica particles and requires six centrifugation steps and five reagents to purify DNA from whole blood.

Specifically, Boom teaches (1) mixing the biological material with a solution consisting of guanidine isothiocyanate, EDTA and Triton X-100, and silica; (2) allowing the nucleic acid to bind to the silica; (3) washing the silica with consecutive washes of guanidine isothiocyanate, ethanol, acetone; and (4) eluting the nucleic acid with an eluent. Disadvantages of this method are the use of a particulate suspension, the use of many centrifugation steps, and the use of hazardous reagents, such as guanidine isothiocyanate and acetone. Furthermore, although this method has been employed successfully for DNA isolation, it is unsuitable for RNA isolation due to unacceptable levels of DNA contamination.

The use of chaotropic salts for the binding and purification of RNA is well known in the art. In another method See U.S. Pat. No. 5,990,302 (Kuroita et al.), the biological material is lysed in an acidic solution containing a lithium salt and a chaotropic agent such as guanidinium isothiocyanate (GITC), after which the RNA is brought into contact with a nucleic acid-binding carrier such as silica. The RNA is subsequently purified by eluting from the silica in a low ionic-strength buffer. This method is disadvantageous in its use of hazardous substances such as the chaotropic salt, guanidine isothiocyanate.

Combinations of chaotropic substances such as guanidine isothiocyanate, guanidine hydrochloride, sodium iodide, and urea mixtures at ionic strengths greater than 4 M in conjunction with silica-based carriers have been taught in the art. For example, Hillebrand et al. See WO 95/34569 describes a one-step method involving a slurry of silica beads to which chaotropic substances are added in order to cause RNA to bind.

The apparent opposite approach to the use of chaotropes is the use of antichaotropes (also known as "kosmotropes" in the art) to isolate DNA. See Hillebrand et al. US 20010041332. Hillebrand describes the use of "antichaotropes", such as ammonium chloride (also cesium, sodium and/or potassium salts are mentioned), in combination with PVP (polyvinyl pyrrolidone) to lyse the starting sample and bind to the solid support with a detergent/alcohol mixture. Besides the fact that it is generally known that cesium and potassium are clearly considered to be chaotropes, due to their low charge density and weak hydration characteristics, while ammonium is considered to be a marginal chaotrope (Collins, K. *Sticky Ions in Biological Systems*, Proc. Natl. Acad. Sci. USA, 92 (1995), 5553–5557; Wiggins, P. M. *High and Low Density Intracellular Water, Cellular and Molecular Biology* 47 (5), 735–744), several disadvantages to the methods of Hillebrand exist. First, the methods use PVP, which has been investigated as a tumorigen. Secondly, heating steps of 65–70° C. are required for lysis and elution. Such heating may cause damage to the nucleic acids by nonspecific degradation or digestion resulting in limited downstream applications, such as incompatibility with restriction digests or blot analysis. Thirdly, the methods described by Hillebrand would not work effectively for isolating RNA because the methods do not employ reagents sufficient to reduce or eliminate RNases that are so troublesome in RNA purification.

Others have taught the use of ion-exchange resins to which nucleic acids bind at low pH and from which they are eluted at a higher pH. See U.S. Pat. No. 5,057,426 (Henco et al.). Such methods are primarily advantageous for the selective separation of long-chain nucleic acids which have a distinctive charge from smaller nucleic acids and other biological materials such as proteins. These methods are not successful for the isolation of RNA (irrespective of length and charge) from the remainder of the biological material. Furthermore, the long-chain nucleic acids must be eluted at high salt concentrations for an ion-exchange method to work. Commonly used salts (e.g., NaCl and KCl) can interfere with many enzymes used in molecular biology.

Polycationic solid supports have also been used in the purification of nucleic acids from solutions containing contaminants. See U.S. Pat. No. 5,599,667 (Arnold et al.). Polycationic supports selectively adsorb nucleotide multimers based on their size, the larger multimers having a higher affinity for the polycationic support than the smaller ones. This method is based largely on the affinity between positively charged cationic solid supports and negatively charged phosphate backbones of nucleotides. Larger nucleotide multimers have higher charges and will consequently bind preferentially over smaller nucleotide multimers. Thus, the method of Arnold is suited to the isolation of nucleotide multimers based on size rather than the isolation of all types of RNA from crude biological materials. Furthermore, the method of Arnold limits itself to the use of polycationic supports composed of cations such as ammonium, immonium and guanidinium ions.

A recent isolation method employs the principle that RNA precipitates preferentially in the presence of guanidinium salts under defined buffer conditions. See U.S. Pat. No. 5,972,613 (Somack et al.). In this method, RNA is precipitated in the presence of guanidinium salts at low temperatures, while the DNA remains in solution. A commonly used method for precipitation of RNA from solution involves the use of LiCl salt. In one version of this method, 0.8 M LiCl is used to selectively precipitate large ribosomal and messenger RNA molecules from a solution containing total RNA molecules (Sambrook, J., Fritsch, E. F., and Maniatis, T. (1989) in Molecular Cloning A Laboratory Manual, Vol. 3, 2nd ed., Appendices E.10 & E.15). In a another version of this method, 2.5 M LiCl is used to selectively precipitate RNA molecules as small as 100 nucleotides in length, from solutions containing total RNA and single nucleotides (Ambion technical bulletin #160).

The method of selectively precipitating RNA from a solution containing nucleic acids and other biological materials is physically different than that of using a solid phase to selectively bind the RNA molecules in a solution. A precipitation event is the reverse of a solution event. Solution involves the dissolving of a solute, such as RNA, by separation of that solute into molecules that are surrounded by solvent. Precipitation involves the removal of solvent and coalescence of individual RNA molecules into a solid which separates from the solvent. These precipitation and solution events occur within a solution environment and do not depend upon a separate and distinct solid phase on which RNA purification and separation occurs.

To further advance the field of RNA purification there is a need for solid phase RNA purification strategies. There is also a need for reagents and methods that are adaptable to solid phase purification strategies which are not only simple and rapid, but general in scope to maximize adaptability for automation. There is a need for reagents that are stable at room temperature (i.e., 20–25° C.), less hazardous (i.e., less corrosive or toxic), nonparticulate to eliminate the need for mixing, and protective of RNA quality. There is also a need for methods with few steps that can be performed using a variety of biological starting materials, whether hydrated or dried, especially as applied to routine testing as found in clinical and research laboratories. In addition the RNA purification reagents must not inhibit subsequent RNA analysis procedures by carrying over particulates or interfering with the buffering capacity or ionic conditions of downstream analyses such as: reverse transcriptase reactions, amplification reactions, nuclease protection assays, northern blotting, and microarray and other labeling reactions.

SUMMARY OF THE INVENTION

It should be noted that the indefinite articles "a" and "an" and the definite article "the" are used in the present application, as is common in patent applications, to mean one or more unless the context clearly dictates otherwise. Further, the term "or" is used in the present application, as is common in patent applications, to mean the disjunctive "or" or the conjunctive "and."

The present invention provides a formulation for isolating and purifying nucleic acids that contains a lithium salt at a concentration of at least about 1 M, a detergent, and a buffer. The formulation may further contain a chelating agent and/or a reducing agent. The formulation of the present invention may lack a chaotrope and/or a strong chaotropic substance. The lithium salt present in the formulation may be lithium chloride. The lithium salt may be present at a concentration of 4–10 M, or at a concentration of 4–8 M. The formulation may have a pH of above about 7, such as between about 7 and about 9 (e.g., a pH of about 8, about 8.5, or about 9). Alternatively, the formulation may have a pH below about 4.5, such below about 3.5.

The detergent in the formulation of the present invention may be an anionic, cationic, zwitterionic or non-ionic detergent. In one embodiment, the detergent is a non-ionic detergent. Examples of appropriate detergents include a tween, triton, nonidet, igepal or tergitol. For instance the detergent may be triton-x. Further, the detergent may be a mixture of triton-x and diethyl glycol monoethyl ether (DGME). In one embodiment the detergent is a mixture of 5% v/v triton-x and 5% v/v DGME. The detergent of the formulation may be present at a concentration of not more than 15% v/v of the final volume of the solution. For example, the detergent may be present at a concentration of about 10% v/v of the final volume of the solution. The buffer of the formulation of the present invention may have a pKa of at least about 8. The chelating agent may be EDTA. The reducing agent may be Tris (carboxyethyl) phosphine (TCEP) or beta-mercaptoethanol (BME). In one embodiment the reducing agent is TCEP. The formulation of the present invention may further contain a tungstate.

In one embodiment of the present invention the formulation for isolating and purifying nucleic acids contains a lithium salt at a concentration of at least about 1 M, a detergent, a buffer, an optional chelating agent, an optional reducing agent, and an optional tungstate, wherein the solution has pH of above about 7.

In another embodiment of the present invention, the formulation for isolating and purifying nucleic acids consisting essentially of a lithium salt at a concentration of at least about 1 M, a detergent, a buffer, an optional chelating agent, an optional reducing agent, and an optional tungstate.

In yet another embodiment, the formulation of the present invention consisting essentially of a lithium salt, a detergent, a buffer, an optional chelating agent, an optional reducing agent, and an optional tungstate, wherein the solution has pH of above about 7.

A further embodiment of the present invention consists essentially of a lithium salt at a concentration of at least about 1 M, a detergent, a buffer, an optional chelating agent, an optional reducing agent, and an optional tungstate, wherein the solution has pH of above about 7.

The present invention also provides methods for purifying substantially pure and undegraded RNA from biological material comprising RNA. In one embodiment the method involves the steps of (a) mixing the biological material, with an RNA Lysing/Binding Solution buffered at a pH of greater than about 7, the RNA Lysing/Binding Solution comprising an RNA-complexing salt; (b) contacting the mixture to a solid support such that nucleic acids comprising substantially undegraded RNA in the mixture preferentially bind to the solid support; (c) washing the solid support with a series of RNA wash solutions to remove biological materials other than bound nucleic acids comprising substantially undegraded RNA, wherein the series of wash solutions comprises a first wash comprising alcohol and an RNA-complexing salt at a concentration of at least 1 M and a second wash comprising an alcohol, buffer and an optional chelator; and (d) preferentially eluting the bound substantially undegraded RNA from the solid support with an RNA Elution Solution in order to obtain substantially pure and undegraded RNA.

The present invention also provides a method for purifying substantially pure and undegraded RNA from biological material comprising RNA, involving the steps of (a) mixing the biological material with an RNA Lysing/Binding Solution, the RNA Lysing/Binding Solution comprising an amphiphillic reagent, and an RNA-complexing salt; (b) lysing the biological material with the RNA Lysing/Binding Solution to form a lysate comprising nucleic acids comprising substantially undegraded RNA and non-nucleic acid biological matter; (c) contacting the lysate to an immobilized solid support such that the nucleic acids comprising substantially undegraded RNA in the lysate preferentially bind to the solid support; (d) washing the solid support with a series of RNA wash solutions to remove biological materials other than bound nucleic acids comprising substantially undegraded RNA, wherein the series of wash solutions comprises a first wash containing alcohol and an RNA-complexing salt at a concentration of at least 1M and a second wash containing an alcohol, buffer and an optional chelator; and (e) preferentially eluting the bound substantially undegraded RNA from the solid support with an RNA Elution Solution in order to obtain substantially pure and undegraded RNA. The RNA Lysing/Binding Solution may be buffered at a pH of greater than about 7.

The Lysing/Binding and/or Wash Solution used in the methods of the present invention formulation of the present invention may lack a chaotrope and/or a strong chaotropic substance. Examples of strong chaotropic substances are guanidinium salts, urea, ammonium, cesium, rubidium, potassium, or iodide salt.

The RNA-complexing salt of the Lysing/Binding and/or Wash Solutions used in the method of the present invention may be an alkali-metal salt, such as a lithium salt. Examples of appropriate lithium salts include lithium chloride or lithium bromide. The RNA-complexing salt of the Lysing/Binding and/or Wash Solution may be present at a concentration greater than about 4 M. In one embodiment, the alkali metal salt may be present at a concentration of between 4–10 M.

The chelating agent used in the methods of the present invention may be EDTA or CDTA.

The biological material used in the method of the present invention may be a crude sample or a partially purified mixture of nucleic acids. Examples of biological materials include a sample of eukaryotic cells, prokaryotic cells, microbial cells, bacterial cells, plant cells, mycoplasma, protozoa, bacteria, fungi, virus, yeast, or rickettsia, or homogenates thereof. Additional examples of biological materials include whole blood, bone marrow, blood spot, blood serum, blood plasma, buffy coat preparation, saliva, cerebrospinal fluid, or solid animal tissue. Further examples of biological materials include feces, urine, tears, or sweat. The biological material may also be an environmental sample taken from air, water, sediment or soil.

The solid support used in the methods of the present invention include components of silica, cellulose, cellulose acetate, nitrocellulose, nylon, polyester, polyethersulfone, polyolefin, or polyvinylidene fluoride, or combinations thereof. The solid support may be contained in a vessel, wherein the vessel is a centrifuge tube, spin tube, syringes, cartridge, chamber, multiple-well plate, or test tube, or combinations thereof.

The substantially pure and undegraded RNA subjected to the methods of the present invention include total RNA (i.e., an mixture of RNA found in a biological material such as all the types of RNA found in a cell), messenger RNA, transfer RNA, ribosomal RNA or viral RNA, or combinations thereof.

The amphiphillic reagent used in the methods of the present invention may be a detergent. The detergent may be a non-ionic detergent, such as a tween, triton, nonidet, igepal or tergitol.

The present invention further provides a method for purifying substantially pure and undegraded RNA from biological material, involving the steps of (a) contacting a biological material containing RNA with a solid support pre-treated with an RNA Lysing/Binding Solution buffered at a pH of greater than about 7 such that the RNA Lysing/Binding Solution is bound to the solid support, the RNA Binding Solution comprising an RNA-complexing salt; (b) contacting the biological material to the solid support such that nucleic acids comprising substantially undegraded RNA preferentially bind to the solid support; (c) washing the solid support with an RNA wash solution to remove biological materials other than bound nucleic acids comprising substantially undegraded RNA; and (d) preferentially eluting the bound substantially undegraded RNA from the solid support with an RNA Elution Solution in order to obtain substantially pure and undegraded RNA.

The present invention further provides a method for purifying substantially pure and undegraded RNA from biological material, involving the steps of (a) contacting a biological material containing RNA, with a solid support pre-treated with an RNA Lysing/Binding Solution buffered at a pH of greater than about 7 such that the RNA Lysing/Binding Solution is bound to the solid support, the RNA Lysing/Binding Solution comprising an amphiphillic reagent and an RNA-complexing salt; (b) contacting the biological material to the solid support in order to release nucleic acids comprising substantially undegraded RNA and non-nucleic acid biological matter causing nucleic acids comprising substantially undegraded RNA to preferentially bind to the solid support; (c) washing the solid support with to remove biological materials other than bound nucleic acids comprising undegraded RNA; and (d) preferentially eluting the bound undegraded RNA from the solid support with an RNA Elution Solution in order to obtain substantially pure and undegraded RNA.

DETAILED DESCRIPTION

The present invention provides reagents, methods, and kits that incorporate a solid support for isolating substantially pure and undegraded RNA from liquid and dried biological samples. The purified RNA is suitable for use in widely used analytical and diagnostic methods such as RT-PCR and microarray analyses that require substantially pure and undegraded RNA.

The present invention provides a combination of unique reagents that may be used to purify RNA from a variety of biological materials without the use of hazardous substances such as phenol, and chloroform, or hazardous chaotropic substances such as guanidinium salts, urea, etc. The series of wash steps taught by the present invention allow effective inhibition of RNase activity, and elimination of residual salts from earlier lysis/binding steps, also without use of hazardous substances.

The reagents taught by the invention include a unique Lysing/Binding Solution, RNA Wash Solutions, and an RNA Elution Solution. These reagents, used in conjunction with an appropriate solid support, are used to generate undegraded RNA, which is substantially pure and contaminant-free.

The RNA Lysing/Binding Solution lyses the biological material while conferring unique binding properties to the nucleic acids released following lysis, such that they preferentially bind to a solid support of choice instead of to contaminants such as proteins, phospholipids, etc. The present invention involves the use of lithium salts, including for example, lithium chloride and lithium bromide. The lithium ion is considered very kosmotropic, due to its high surface charge density and strong hydration characteristics. The lithium ion is unique in that it has a small radius, in comparison to that of sodium, potassium, rubidium and cesium ions also found in the alkali metal group. This causes its surface charge density to be larger than the other ions in this group. The larger surface charge density is responsible for the tremendous interaction of the lithium ion with water molecules. This causes water molecules to organize around the ion and to maintain this structured effect even past the first hydration shell.

The Lysing/Binding Solution of the present invention contains a lithium salt so that RNA binds to a distinct solid phase through an adsorption mechanism. The use of lithium salt to cause adsorption of RNA to a solid phase differs from the use of lithium for the precipitation of RNA. In the adsorption process, the solvent molecules are separated from the RNA molecules. The interaction between the RNA and the solid phase, however, is energetically more favorable than that of RNA molecular interactions, so that adsorption to the solid phase occurs instead of precipitation. An example of an appropriate solid phase is borosilicate.

The RNA Lysing/Binding Solution of the present invention achieves preferential binding to a solid support by the presence of an RNA-complexing salt, such as lithium chloride or lithium bromide, in a buffer, and an amphiphillic reagent, without the use of hazardous chaotropic substances such as guanidinium salts, urea, etc. The lithium ion binds to the charged phosphate backbone of nucleic acids such as RNA, causing the RNA to be less soluble at high lithium ion concentrations (Kazakov S. A., *Nucleic Acid Binding and Catalysis by Metal Ions*, in Bioorganic Chemistry: Nucleic Acids, Ed. Hecht, S. M., Oxford University Press, NY & Oxford, 1996).

The present invention teaches the use of a unique low or neutral to high pH RNA Lysing/Binding Solution, for maximum RNA yield from various sample types. The RNA Lysing/Binding Solution may be buffered to maintain the pH at least about 7 (such as a pH of at least about 8, at least about 8.5, or at least about 9). The RNA Lysing/Binding Solution comprises a buffer to adjust the pH as desired. The buffer may have a pKa of at least about 8. In one embodiment the buffer is tris(hydroxymethyl)aminomethane (Tris). It is observed that RNase enzymes are very active at pH values of about 5–6. For many RNase enzymes, pH 6.0 has been observed to be the optimum pH for activity due to the presence of one protonated and one deprotonated histidine residue required for activity at this pH. The pH of the present Lysis/Binding Solution may be low, such as below about 4.5, or even below pH 3.5 in order to minimize or eliminate RNase activity; however, RNA yields are about 4–5 times less than at more alkaline pH values.

Suitable RNA-complexing salts for the present invention include those that contain the alkali metal ions such as lithium, sodium, potassium, rubidium and cesium, since all of these cations complex specifically to the phosphate groups of the RNA molecules. This complexation and subsequent neutralization of the RNA molecule cause the RNA molecules to become less stable in the aqueous environment and promote binding to the solid phase. One embodiment of the present invention is to use a lithium salt. Lithium salts used to practice the present invention include, but are not limited to, lithium chloride and lithium bromide. Lithium fluoride and lithium iodide are less desirable alkali salts because their cost is about five times the cost of the lithium chloride and bromide salts. In addition, lithium ion is the only clearly kosmotropic ion in the aforementioned list. The sodium ion is a borderline kosmotrope, while potassium, rubidium and cesium ions are chaotropic ions (Collins, K. *Sticky Ions in Biological Systems*, Proc. Natl. Acad. Sci. USA, 92 (1995), 5553–5557). Cesium chloride costs about five times more than the other alkali metal chloride salts and has more limited solubility behavior than the lithium chloride and bromide salts. In addition, sodium, potassium and ammonium chloride salts have much more limited solubility behavior as compared to the lithium chloride and bromide salts, as exhibited by the large exothermic heats of solution exhibited by lithium salts in water (CRC Handbook of Chemistry and Physics, 62nd edition, CRC Press, Boca Raton, Fla.).

Preferential binding of RNA to a solid support is enhanced by high concentrations of alkali metal salts. The alkali-metal salt may be at a concentration of between 4–10 M. In addition, high metal salt concentrations are required in order to maintain RNA binding and completely eliminate RNase activity in the Wash I Solution.

In Example 2, it is observed that in the Lysis/Binding Solution, ammonium and potassium chloride salts have maximum solubilities of 3M and <3M respectively, while cesium and sodium chloride salts readily dissolve to 4M. As can be seen in Table 2, these salt values approximately match those expected in aqueous solution, except for that of ammonium chloride (CRC Handbook of Chemistry and Physics, 62nd edition, CRC Press, Boca Raton, Fla.). The limited solubility for ammonium chloride salt may be due to the presence of Triton X-100 and DGME in the Lysing/Binding Solution. In Example 7, it is shown that when these salts (potassium chloride was not used due to its limited solubility) are used to purify RNA from pig spleen, the RNA yields are 3–5 times less than when the lithium salts, lithium chloride or bromide, are used for Lysing/Binding. The cesium, ammonium and sodium chloride lysates were gelatinous in nature and it is suspected that homogenization and lysing are not as complete when using these salts, as when the lithium salts are used, thus resulting in more gelled particulates and lower RNA yields. The lithium chloride and bromide lysates are fluids which are readily used in the following purification steps, whereas the other salts lysates cannot be manipulated easily due to their gelatinous nature. Even though most of the salts studied were soluble near or at 4M in concentration, they did not provide for effective lysing or homogenization of tissue samples, and so were ineffective with regard to sample manipulation and RNA yield recovery.

In Example 2, it is shown that the maximum solubilities for cesium, ammonium, sodium and potassium chloride salts in the Wash I Solution containing 55% ethanol, are much less, at 2.5 M, 2 M, 1.5 M and <1 M, respectively. The RNA yields obtained from the purifications utilizing these solutions were also less, by ⅓–½, as compared to the purifications in which 5M lithium chloride or bromide were used instead. In previous work, 2.5 M LiCl Wash I Solutions proved to be ineffective against RNase activity, since it was showing degraded RNA in the final eluted RNA product. Further experimental work demonstrated that at least 5 M LiCl was needed in the Wash I Solution to be most effective. Since the solubilities of the aforementioned salts in ethanol is much more limited than that of the lithium salts, it is suspected that RNase activity would also be more prevalent than with the lithium salts.

Alkaline earth metal salts containing the kosmotropic magnesium and calcium ions, although also having properties of forming salt complexes with RNA, are not functional for use in RNA purification strategies since they catalyze the cleavage of internucleotide phosphodiester bonds in RNA molecules (Kazakov S. A., *Nucleic Acid Binding and Catalysis by Metal Ions*, in Bioorganic Chemistry: Nucleic Acids, Ed. Hecht, S. M., Oxford University Press, NY & Oxford, 1996). In addition, for example, the alkaline earth metal beryllium is about 20 times more expensive than for the alkaline metal salts lithium chloride or lithium bromide, and therefore is not as practical for use in the present invention.

In one embodiment, the amphiphillic reagent in the RNA Lysing/Binding Solution is a detergent, a surfactant, or a mixture thereof, that aids in lysing the biological material. The detergent is present in order to solubilize membrane components, such as lipids and proteins, in order to facilitate the lysis of cell membranes and the homogenization process. The surfactant is present in order to assist in the solubility of the solution as well as help increase shelf-life of the solution. The detergent or surfactant may be anionic, cationic, zwitterionic or nonionic. In one embodiment, a nonionic detergent is used. It has been observed that some charged detergents such as SDS, do not remain solubilized in higher concentration salt solutions and in fact, they may tend to precipitate rather quickly. It is possible however, to use such charged detergents under certain experimental conditions, including but not limited to those described in one embodiment of the present invention, for pre-treating the solid support.

Examples of non-ionic detergents include detergents from the Tween, Triton, Tergitol and Nonidet or Igepal classes of detergents. In one embodiment the surfactant is DGME (diethyl glycol monoethyl ether). The combination of the lithium salt and a detergent or surfactant, each at the aforementioned high concentrations in a neutral to high pH buffer, also serve to denature enzymes such as RNases, which are generally associated with biological material. Optionally, the RNA Lysing/Binding Solution may also contain a chelating agent to complex extraneous metal ions, and a reducing agent to reduce disulfide bonds found in certain RNase enzymes, in order to completely denature them.

The invention also incorporates the use of an RNA wash series to most effectively remove impurities such as proteins and phospholipids from the solid support while allowing the nucleic acids to remain bound to the solid support. The wash series includes a Wash I Solution containing an alkali metal salt, such as lithium salt at about 5M and an alcohol, such as ethanol at about 55%. The high lithium salt concentration in the Wash I Solution is an important part of the wash series. Its primary purpose is to ensure a complete and thorough elimination of RNase enzyme activity of RNase enzymes that nonspecifically adsorb onto the solid support material from the initial lysate passing through the solid phase material just prior to the Wash I step. The high concentration of lithium salt present in both the Lysing/Binding Solution and the Wash I Solution provides a dual purpose. First, the high concentration of lithium salt imparts effective RNase denaturation properties to the solutions. For example, high concentrations of lithium chloride salt have been shown to effectively denature RNase A (Ahmad, F., *Free Energy Changes in Ribonuclease A Denaturation*, J. Biol. Chem., 258, 18 (1983) pp. 11143–11146; Ahmad, F., Free Energy Changes in Denaturation of Ribonuclease A by Mixed Denaturants, J. Biol. Chem., 259, 7 (1984) pp. 4183–4186). Secondly, while high lithium concentrations cause binding from the Lysing/Binding Solution, the bound RNA is retained on the solid phase during the use of the Wash I Solution and used in combination with the ethanol.

The Wash II Solution (which contains ethanol, EDTA and Tris buffered at a neutral pH of 6–8) is used subsequent to the Wash I Solution in order to wash away remaining lithium salt from the bound RNA and solid phase material. This prevents the final eluted RNA product from containing inhibitory concentrations of salt ions in downstream applications. It has been reported that the chloride ion, in particular due to use of LiCl as a precipitant, may inhibit reverse transcription by suppressing the activity of RNA dependent DNA polymerases (Sambrook, J., Fritsch, E. F., and Maniatis, T. (1989) in Molecular Cloning A Laboratory Manual, Vol. 3, 2nd ed., Appendices E.10). This, however, has not been observed using the solution formulations taught in the present invention, since the Wash II Solution, used to wash the solid phase material twice prior to elution, appears to eliminate chloride contamination of the eluent. The present RNA purification method can be used to purify RNA to be used for microarray technology. (See Example 8 below.)

The simplicity and efficiency of the RNA Lysing/Binding Solution, and RNA Wash Solutions in conjunction with an appropriate solid support results in the use of a simple RNA Elution Solution such as RNase-free water or DEPC treated water.

The present invention also teaches methods for the isolation of RNA from biological material. The biological material includes, for example, cell or viral suspensions, body fluids and wastes, whole blood, bone marrow, buffy coat, plasma, cultured cells, all suspensions (e.g., bacteria, tissue homogenates), crude or partially purified mixtures of nucleic acids, and environmental samples. The environmental samples include, for example, air, water or soil.

The versatility and effectiveness of the RNA Lysing/Binding Solution lends itself to two viable alternative methods for RNA isolation. In the first method, the biological material is contacted with the RNA Binding/Lysing Solution before it is contacted with the solid support. In one embodiment, when the biological material comprises cellular or viral material, the RNA Lysing/Binding Solution is used to lyse the cells and release the nucleic acids, including RNA. In the second method, the RNA Lysing/Binding Solution is added directly to the solid support and allowed to bind to the solid support, thereby eliminating a step, and further simplifying the method. In this latter method, the RNA Lysing/Binding Solution is directly applied to the solid support and then dried on the solid support before contacting the biological material with the treated solid support.

Suitable solid supports include silica-based supports such as glass fiber, or other materials such as cellulose, cellulose acetate, nitrocellulose, nylon, polyester, polyethersulfone, polyolefin, polyvinylidene fluoride, and combinations thereof. The solid support may be encased or immobilized in a vessel to enable plug-flow or continuous-flow RNA isolation methods. Alternately, the material of the solid support may be packed so as to create a free-standing solid support such as a membrane, disk, or cylinder that may be immobilized or encased in a suitable vessel, such as a tube or plate. In one embodiment, the solid support may be fibrous or particulate to allow optimal contact with the biological material.

The present invention also provides kits for purifying RNA comprising instruction means for preparing substantially pure and undegraded RNA from a biological sample and one or all of the following: RNA Lysing/Binding Solution, either as a separate solution or pretreated onto a solid support, a solid support either untreated or treated with an RNA Lysing/Binding Solution, RNA Wash Solutions, an RNA Elution Solution or any combination thereof. In addition, the kit can include auxiliary components such as a proteinase K solution and a pre-clear column for use with tissue samples, a vessel to contain the solid support, vessels to contain substantially pure and undegraded RNA, and combinations thereof. Substantially pure, undegraded RNA is RNA that is suitable for use in subsequent analyses known to those with skill in the art, for example, RT-PCR, in vitro translation, northern blotting, microarray analysis etc.

The present invention provides reagents, methods and kits for purifying RNA from biological samples. Such biological samples include biological material, typically in an aqueous mixture or dried, that contains RNA, including complex biological mixtures of prokaryotic or eukaryotic cells. The methods and kits of the present invention isolate a wide range of RNAs. Candidate RNAs include, but are not limited to, ribosomal RNA, messenger RNA, transfer RNA, and viral RNA, or combinations thereof, all of which can be recovered over a wide molecular weight range. Typically, the biological material also contains DNA, carbohydrates, proteins, and lipids. Biological materials include, but are not restricted to the following: body fluids such as whole blood, bone marrow, blood spots, blood serum, blood plasma, buffy coat preparations, saliva and cerebrospinal fluid, buccal swabs, cultured cells, cell suspensions of bacteria or tissue homogenates, solid animal tissues such as heart, liver and brain, body waste products, such as feces and urine, environmental samples taken from air, water, sediment or soil, plant tissues, yeasts, bacteria, viruses, mycoplasmas, fungi, protozoa, rickettsia, and other small microbial cells. Lysates, homogenates, or partially purified samples of these biological materials may also be used. In one embodiment, the biological material is crude or partially purified mixtures of nucleic acids.

The reagents, methods and kits of the present invention provide substantially pure and undegraded RNA with relatively little contaminating genomic DNA or other impurities such that the RNA may be used in downstream processes such as RT-PCR and microarray analyses. As used herein, "substantially pure" means substantially free of genomic DNA, carbohydrate, protein, lipid impurities, such that the RNA can be used in subsequent analyses known to those with skill in the art such as RT-PCR and microarray analyses. As used herein, "substantially undegraded" RNA means nondigested or intact RNA, which can be readily determined by one of skill in the art using standard techniques. That is, the RNA is not damaged by enzymatic, physical or chemical means during the purification methods of the present invention.

The reagents, methods and kits of the present invention may be used to isolate substantially pure and undegraded RNA over a wide range of biological sources, and life forms, all of which can be recovered over a wide molecular weight range. The substantially pure and undegraded RNA obtained from practicing the invention can also be evaluated for purity, yield, size, reverse transcriptase or other hybridization processes, amplification, hybridization ability, etc. The substantially pure and undegraded RNA is representative of the total RNA found in the biological sample, and is typically a combination of, but not restricted to, mRNA, tRNA, rRNA, and viral RNA.

The biological samples include, for example, cell or viral suspensions and pellets thereof, body fluids, and tissue homogenates, etc. If the biological sample consists of cells or viruses, the cells or viruses may be enumerated. The enumeration may be conducted using standard cell counting methods such as an electronic cell counter (e.g., CBC5 Coulter Counter, Coulter Corp., Hialeah, Fla.) or a visual counting chamber (e.g., a hemacytometer, Bright Line, American Optical, Buffalo, N.Y.).

1. Reagents: The present invention discloses three categories of reagents. These are RNA Lysing/Binding Solutions, RNA Wash Solutions, and RNA Elution Solutions.

(i) RNA Lysing/Binding Solution: An RNA Lysing/Binding Solution allows nucleic acids to preferentially bind to a solid support of choice, enables efficient lysis of the biological sample to release the nucleic acids, and effectively inhibits RNase activity. An RNA Lysing/Binding Solution of the present invention has the following components: a buffer; a lithium salt; an amphiphillic reagent, such as a detergent or surfactant or mixture thereof; and optionally chelating, reducing, and tungstate reagents. An RNA Lysing/Binding Solution of the present invention is unique in that it requires no added strong chaotropic substances such as guanidinium salts, urea, etc. Guanidinium salts and urea are strong chaotropic salts that disrupt the structure of water and thus tend to decrease the strength of hydrophobic interactions resulting in a drastic effect on other solute molecules. For example, urea, when dissolved in water, disrupts the secondary, tertiary, and quaternary structures of proteins, and subsequently causes dissociation of proteins from RNA. Guanidinium salts and urea dissolve in water through endothermic reactions. Both guanidinium salts and urea are considered to be strongly chaotropic salts as defined by the Hofmeister series, a widely used system that ranks cations and anions according to relative chaotropic strength (F. Hofmeister, *On the understanding of the effects of salts*, Arch. Exp. Pathol. Pharmakol. (Leipzig) 24 (1888) 247–260).

Unlike strong chaotropic salts, the reaction of lithium salts (such as lithium chloride and lithium bromide) in water is an exothermic reaction and is indicative of the tremendous ion-dipole interaction exhibited by the strong kosmotropic lithium ion and the resulting large solubility. Differences such as these are indicative of the differences between the strong chaotropic substances, such as guanidinium salts, and the alkali-metal salts, especially lithium chloride, of the present invention.

The first component of the RNA Lysing/Binding Solution is a buffer that maintains the pH of the solution. For example, the pH may be at least about 8, at least about 8.5, or even at least about 9. The buffer may have a pKa of at least about 8, and may be used at a concentration of 10–100 mM. An example of an appropriate buffer is Tris buffer. Optionally, a base may be used to adjust the pH of the RNA Lysing/Binding Solution. The base may be one that can raise the pH of the solutions to no less than 7. The base may be an alkali-metal hydroxide. Such alkali-metal hydroxides include sodium hydroxide, potassium hydroxide, and lithium hydroxide.

The second component of the RNA Lysing/Binding Solution is an RNA-complexing salt that confers unique binding properties to nucleic acids, such as RNA, such that the nucleic acids can preferentially bind to the solid support over other contaminants such as proteins, phospholipids, etc.

For example, such an RNA-complexing salt may be a lithium salt, such as lithium chloride or lithium bromide. The salt may be present at a concentration of between 4–10 M, because preferential binding of RNA to a solid support is enhanced by high concentrations of alkali-metal salts.

The RNA Lysing/Binding Solution additionally comprises one or more amphiphillic reagents. An amphiphillic reagent comprises a compound or molecule having a hydrophilic group attached to a hydrophobic functionality such as a hydrocarbon chain and having surfactant properties. In one embodiment, the amphiphillic reagent is a detergent. Although anionic, cationic, and zwitterionic detergents may all be used, RNA isolation is optimally achieved through the use of a non-ionic detergent. Although any nonionic detergent may be used, examples of non-ionic detergents are those from the Tween class (Tween-20, Tween-40, Tween-60, Tween-80, etc.), the Triton class (X-100, X-114, XL-80N, etc), Tergitols (XD, TMN-6, etc.) and Nonidets or Igepal (NP-40, etc.). The nonionic detergent may be used at a concentration of 5–15%, such as at about 10%. In another embodiment, the amphiphillic reagent is a surfactant, such as DGME (diethylene glycol monoethyl ether). The surfactant may be used at a concentration of 5–15%, such as at about 10%. In yet another embodiment, a combination of detergents and surfactants may be used. In one embodiment, a combination of detergent and surfactant Triton-X and DGME is used. The combination may be at a concentration of 5–15%, such as at about 10%. In one example, the combination is 5% Triton-X and 5% DGME.

In order to prevent degradation of the RNA, RNase-free water is used in the RNA Lysing/Binding Solution. Optionally, a chelating agent may also be used in either solution to prevent degradation of contaminating DNA. The use of a chelating agent prevents DNA polymers from being degraded to smaller fragments which may cause additional contamination problems. The chelating agent may be present at a concentration of 1–100 mM, or at a concentration of 1–10 mM. Examples of chelating agents are EDTA or CDTA. Optionally, a reducing agent may be added to the kit and is used to reduce the disulfide bonds in RNases. This may be a necessary addition for high RNase-containing tissues, for example, spleen and pancreas. The reducing agent may be TCEP (Tris (carboxyethyl) phosphine) or β-ME (β-mercaptoethanol). In one embodiment, the reducing agent is TCEP. The concentration of the reducing agent may be 1–100 mM. In one embodiment, the reducing agent is present at a concentration of 10–50 mM. Also optionally, a tungstate component, for example sodium tungstate, may be added to the Lysing/Binding Solution. Tungstate may be a necessary component when using certain supports, such as the solid supports made from cellulose. Although its exact function with these supports is unknown, it appears to help deproteinate or deglycosylate the tissue sample lysates and allow nucleic acid binding. Cultured cells typically do not have such high levels of structural and metabolic proteins and thus isolation from cell samples is not necessarily improved by use of tungstate. Tungstate does however appear to aid particularly in the isolation of nucleic acids from animal tissue.

The RNA Lysing/Binding Solution of the present invention possesses significant advantages over other described reagents. The unique combination of a high concentration of an RNA-complexing lithium salt and a high concentration of a detergent in a neutral- to high-pH buffer inactivates enzymes harmful to RNA (such as RNases) without the use of such reagents as phenol, chloroform, and guanidinium salts. Additionally, the solution confers a high binding property to the nucleic acids such that they tightly bind with the solid support of choice.

(ii) RNA Wash Solutions: The present invention also teaches a series of powerful RNA wash solutions to wash the solid support to which nucleic acids are bound so as to rid it of non-nucleic acid contaminants such as proteins, phospholipids, etc. The RNA wash solutions may contain an alcohol at a concentration greater than 50%.

The Wash I Solution contains a high salt concentration, such as a lithium salt (e.g., lithium chloride). The lithium salt concentration may be at 4–10 M, such as at 5–8 M. For the purposes of the present invention, the high salt concentration means a salt concentration high enough to inhibit RNase activity, and to complex to and provide a salting-out affect for binding of RNA to the solid phase. The Wash I Solution additionally contains an alcohol (e.g., ethanol). The alcohol concentration is at 50–80%, such as at 55–65%.

The Wash II Solution contains a buffer, alcohol, and optional chelator (EDTA). For purposes of the present invention, the Wash II Solution provides for a final wash to remove any residual biological material. The buffer composition may be Tris HCl, such as at pH 6–8. The buffer concentration may be at 50–150 mM (e.g., at 100 mM). The alcohol may be ethanol. The alcohol concentration may be at 50–90% (e.g., at 70%). The EDTA concentration may be at 1–20 mM (e.g., at 5–10 mM).

(iii) RNA Elution Solution: RNA bound to the solid support may be eluted using an RNA Elution Solution. The simplicity of the reagents used in lysing the biological material and binding of the RNA to the solid support, and in washing the solid support taught by the present invention lends itself to a simple RNA Elution Solution. In one embodiment, RNase-free water may be used. For example, the water may be treated with a substance that inactivates RNases, such as diethyl pyrocarbonate (DEPC). Other RNA Elution Solutions known to those skilled in the art may also be used. For example, an RNA Elution Solution that may be used is Gentra Solid Phase RNA Elution Solution (Gentra Systems, Inc., Minneapolis, Minn.).

2. Solid Support: A variety of solid supports may be used in the present invention. These include silica-based solid supports and solid supports made of cellulose, cellulose acetate, nitrocellulose, nylon, polyester, polyethersulfone, polyolefin, polyvinylidene fluoride, and combinations thereof. The size of the solid support suitable for use with the reagents of this invention may vary according to the volume of biological material. For example, glass fiber membranes may be cut to different sizes, in order to allow for the binding, purification and elution of different quantities of RNA.

In one embodiment, the solid support may be a material that permits the preferential binding of nucleic acids to the solid support instead of other biological contaminants in the presence of the aforementioned RNA Lysing/Binding Solution described above. Such a solid support may be a silica-based or borosilicate glass fiber material. Glass fiber materials provide a better yield because of the specific binding properties to the electropositive silicon and boron atoms, and because of hydrogen bonding properties of the silicate surface. Because of the specificity of silica for nucleic acids, more RNA is bound relative to other contaminants and the eluted product is made more substantially pure.

The shape of the solid support suitable for use with the reagents of this invention may be, for example, a sheet, a precut disk, cylinder, single fiber, or a solid support composed of particulates. The material of the solid support may be packed so as to create a free-standing solid support such as a membrane, disk, or cylinder that may be immobilized or encased in a suitable vessel. If necessary, the solid support is contained in an appropriate vessel, e.g., a paper form (such as a Guthrie card), a microcentrifuge tube, a spin tube, a 96-well plate, a chamber, or a cartridge. If the solid support comprises fibers, it may be encased in a suitable vessel so as to pack the fibers appropriately, allow for optimal nucleic acid binding, and the washing away of contaminants such as protein, phospholipids, etc.

In one embodiment, the solid support may be pre-treated with the RNA Lysing/Binding Solution to reduce the number of steps for RNA isolation and to lyse the biological material and bind the nucleic acids in a single step. In one embodiment, the volume of the RNA Binding/Lysing Solution used to treat the solid support is at least one-tenth of the total volume of the solid support. In another embodiment, the volume of the RNA Binding/Lysing Solution is at least half the total volume of the solid support, or the volume of the RNA Binding/Lysing Solution corresponds to the total volume of the solid support. The total volume of the solid support refers to the volume defined by the external boundaries of the solid support. The external boundaries may be dictated by the shape and/or internal boundaries of the vessel containing the solid support. The Lysing/Binding Solution may be bound covalently, non-covalently, by being trapped within the interstitial spaces of the solid support, or by being deposited on the material (e.g., fibers, beads, etc.) of the solid support. In one embodiment, the RNA Binding/Lysing Solution is allowed to dry on the solid support.

In another embodiment of the invention, the RNA Binding/Lysing Solution may be added directly to the material (e.g., fibers, etc.) used in making the solid support and may be allowed to dry before it is made into the final user-ready form (e.g., paper, swab, disk, plug, column, etc.).

In order that the invention may be better understood, specific embodiments for vessels that contain the solid support will now be described in more detail.

In one embodiment of this invention, the vessel is a cartridge equipped with one or more inlet ports or pierceable septa at the top. The inlet ports are attached to vessels upstream containing the sample or reagents through a connector, such as a female Luer-Lock. One inlet, the sample port, is used for the application of the biological sample to the solid support. An optional feature on the sample port is a self-sealing mechanism that seals the sample port after sample has been transferred through it. The second inlet serves as a reagent port. An optional feature on both inlet ports is a protective breakaway seal. Furthermore, the inlet ports, breakaway seals and diffuser may be housed in an optional screw-cap. At the bottom of the solid support is an optional diffuser with a pore size suitable for the dispersion and passage of cellular debris, proteins and lipid molecules. The diffusers allow for a uniform traversal of biological material across the cross section of the cartridge, and prevent unequal buildup of biological material anywhere above or below the solid support. The outlet of the cartridge comes equipped with a protective cap that fits neatly over the tapered barrel. The purified RNA is collected in a collection tube that consists of a conical tube with a snap cap for easy and contamination-free storage. The entire vessel can be scaled in size depending on the size of the samples to be processed and the yields needed for subsequent analysis.

In another embodiment of this invention, the vessel is a spin tube designed to hold an insert into which the solid support is packed. The solid support may be silica-based, cellulose, cellulose acetate, nitrocellulose, nylon, polyester, polyethersulfone, polyolefin, polyvinylidene fluoride, and combinations thereof. In one embodiment, the support is a silica-based borosilicate glass fiber membrane. The insert has a flanged top to hold it in the spin tube and a perforated bottom to allow fluids to pass through while supporting the solid support. A cap tethered to the spin tube may be used to cover the insert. Solutions, for instance, RNA Lysing/Binding Solution containing non-nucleic acid contaminants, RNA Wash Solutions, or RNA Elution Solution containing RNA, pass through the perforated bottom and are collected at the bottom of the spin tube by centrifugal forces that draw out the solutions.

In yet another embodiment, the vessel may be multiple well plates, for example, 6, 12, 24, 48, 96, or 384 well plates where a solid support is packed into each well. The bottom of each well has an exit port through which solutions containing contaminants or purified RNA can pass.

The unique combination of the solid support of choice with the unique reagents—RNA Lysing/Binding Solution, RNA Wash Solutions, and RNA Elution Solution—results in the isolation of substantially pure, undegraded RNA. The properties of the RNA Lysing/Binding Solution as described above permit preferential binding of the nucleic acids to the solid support, while the RNA Elution Solution permits the preferential elution of the RNA from the solid support.

3. Methods: The present invention also provides methods for purifying RNA from biological material. The reagents and solid supports taught in the invention lend themselves to two alternate isolation methods. In the first method, the biological material is contacted with the RNA Lysing/Binding Solution before it is contacted with the solid support. The RNA Lysing/Binding Solution is used to lyse the biological material and release the RNA before adding it to the solid support. Additionally, the RNA Lysing/Binding Solution prevents the deleterious effects of harmful enzymes such as RNases. The RNA Lysing/Binding Solution may be successfully used to lyse cultured cells or white blood cells in pellets, or to lyse cells adhering to or collected in culture plates, such as standard 96-well plates. If the biological material is composed of tissue chunks or small particles, the RNA Lysing/Binding Solution may be effectively used to grind such tissue chunks into a slurry because of its effective lysing capabilities. The RNA Lysing/Binding Solution volume may be scaled up or down depending on the cell numbers or tissue size. Once the biological material is lysed, the lysate may be added directly to the solid support or may be put through a pre-clear membrane to eliminate large particulates from the lysate. An example of an appropriate product is the Gentra Solid Phase RNA Pre-Clear Column (Gentra Systems, Inc., Minneapolis, Minn.).

In the second method, the RNA Lysing/Binding Solution may be added directly to the solid support, thereby eliminating a step, and further simplifying the method. In this latter method, the RNA Lysing/Binding Solution may be applied to the solid support and then dried on the solid support before contacting the biological material with the treated solid support. For example, in one embodiment, a suitable volume of RNA Lysing/Binding Solution is directly added to a solid support placed in a Spin-X® basket (Costar, Corning N.Y.) which is further placed in a 2 ml spin tube. The solid support is heated until dry for at least 12 hours at a temperature of between 40–80° C., after which any excess unbound RNA Lysing/Binding Solution is removed, and is then stored under desiccation. The biological material may be directly added to the solid support pre-treated with the RNA Lysing/Binding Solution, and allowed to incubate for at least one minute, such as for at least 5 minutes, until it is suitably lysed and the nucleic acids are released, and bound to the solid support.

When the biological materials comprise cellular or viral materials, direct contact with the RNA Lysing/Binding Solution, or contact with the solid support pre-treated with the RNA Lysing/Binding Solution causes the cell and nuclear membranes, or viral coats, to solubilize and/or rupture, thereby releasing the nucleic acids as well as other contaminating substances such as proteins, phospholipids, etc. The released nucleic acids, selectively bind to the solid support in the presence of the RNA-complexing lithium salt. Having the optional reducing agent helps provide for reduction in RNase activity, which may be necessary in high RNase-containing tissues (for example, spleen and pancreas).

After, this incubation period, the remainder of the biological material is optionally removed by suitable means such as centrifugation, pipetting, pressure, vacuum, or by the combined use of these means with an RNA wash solution such that the nucleic acids are left bound to the solid support. The remainder of the non-nucleic acid biological material which includes proteins, phospholipids, etc., may be removed first by centrifugation. By doing this, the unbound contaminants in the lysate are separated from the solid support. The multiple wash steps rid the solid support of substantially all contaminants, and leave behind RNA preferentially bound to the solid support.

Subsequently, the bound RNA may be eluted using an adequate amount of an RNA Elution Solution known to those skilled in the art. The solid support may then be centrifuged, or subjected to pressure or vacuum, to release the RNA from the solid support and can then be collected in a suitable vessel.

As another aspect of this invention, a kit is provided that includes specific protocols, which in combination with the reagents and optionally the solid supports described herein, may be used for purifying RNA from biological materials according to the methods of the invention. This invention will be further described by reference to the following detailed examples. These examples are offered to further illustrate the various specific and illustrative embodiments and techniques. It should be understood, however, that many variations and modifications may be made while remaining within the scope of the present invention.

All of the raw materials mentioned below are readily available from commercial sources such as Sigma Chemical Company, St. Louis, Mo. All percentages are in volume per volume, based on the total volume of the reagent, unless specified otherwise.

EXAMPLE 1

Cost Analysis

In order to produce the best quality solid phase RNA purification product, the product must function exceptionally well in several respects. The solid phase RNA purification product must effectively isolate a pure RNA sample from a variety of sample types and result in the highest possible yields of RNA. It must be user friendly, meaning the steps must not be too onerous, and the components must not be toxic and can be disposed of easily. Further, the product must be economical for the user. Therefore, finding cost effective components for the solutions was essential. Table 1 shows the cost for each of the salts evaluated herein.

TABLE 1

Cost

| Salt | Amount (grams) | Cost ($) |
|---|---|---|
| BeCl$_2$ | 25 | 600.00 |
| CaCl$_2$ | 500 | 105.00 |
| CsCl | 500 | 340.00 |
| KCl | 500 | 30.00 |
| LiBr | 500 | 65.00 |
| LiCl | 500 | 60.00 |
| LiF | 50 | 400.00 |
| LiI | 250 | 330.00 |
| MgCl$_2$ | 500 | 50.00 |
| NaCl | 500 | 24.00 |
| NH$_4$Cl | 500 | 22.00 |

Although the lithium salts work well for the methods of the present invention, the lithium salts LiF and LiI are expensive, and additionally, LiF is quite hazardous. LiCl and LiBr both work well with the methods of the present invention and cost about the same at $60–65 per 500 grams. KCl, NaCl, and NH$_4$Cl are all economical, but do not result in the RNA yields desired. See Examples 2 and 7 below.

EXAMPLE 2

Solubility and Heat of Solution Data for Chloride Salts and Compared to LiCl and LiBr Salts for Solid Phase RNA Purification Procedure The solubility and performance of several chloride salts was examined and compared to two lithium salts, lithium chloride and lithium bromide. The Lysing/Binding Solution and Wash I Solutions were both prepared using other chloride salts, in order to examine maximum solubility obtainable in both the buffer and detergent based Lysing/Binding Solution, and the ethanol based Wash I Solution. Table 2 shows the approximate maximum solubility as measured in this work and compares it to tabulated solubility data extrapolated to 20° C., as well as tabulated heat of solution data as obtained from the Handbook of Chemistry and Physics (62nd edition, CRC Press, Boca Raton, Fla.).

The solubility of most of the chloride salts studied in the Lysis/Binding Solution, were comparable to the lithium chloride and bromide salts at a concentration of 4 M, except for those of potassium chloride and ammonium chloride. The expected solubility of potassium chloride was low, when compared to the solubility of the other salts, at only approximately 3 M in aqueous solution. The other salts were expected to be more soluble than 4 M in aqueous solution, however it was observed that the ammonium chloride salt is only soluble to approximately 3 M, when compared to the expected solubility of about 7 M. This could be due to the presence of Triton X-100 (5%) and DGME (5%) in solution, since the combination for these components in solution was 10%. Except for the salts, the remainder of the Lysing/Binding Solution was kept constant within all solutions and contained, 5% Triton X-100, 5% DGME (diethylene glycol monoethyl ether), 10 mM EDTA, 10 mM TCEP, 1% sodium tungstate, in 100 mM TRIZMA at pH 8.8.

The solubility of all other chloride salts measured here were significantly lower in the Wash I Solution, than for the lithium salts, lithium chloride and bromide. For cesium, ammonium, sodium and potassium chloride salts, the maximum solubilities obtained in 55% ethanol were about 2.5 M, 2 M, 1.5 M, and <1 M, respectively. This is significantly lower than the 5 M at which the LiCl and LiBr solutions were prepared for purification use. At 2.5 M LiCl Wash I Solution, RNase activity was detected at least half of the time, as degraded RNA in the final eluted RNA product. Further experimental work demonstrated that at least 5 M LiCl was needed in the Wash I Solution in order to eliminate the RNase activity. It is likely that RNase activity would be detected using the LiCl and LiBr salts as well, at least some proportion of the time, and depending upon the tissue from which the RNA is purified. As shown in Table 2, the solubilities of the salts observed for Wash I match those predicted for pure alcohol or ethanol for the lithium chloride and bromide salts, and for sodium chloride. However, the predicted solubilities varied somewhat from those demonstrated here for the cesium, ammonium and potassium salts. This is probably because solubility definitions are somewhat vague for predicted alcohol solubilities, and the Wash I Solution used in this experiment contained a mixture of water and ethanol, rather than a pure alcohol solution.

The large exothermic heats of solution for lithium chloride and lithium bromide in water provided substantiation as to the large solubilities demonstrated by lithium salts in general. The other chloride salts in this example exhibited endothermic heats of solution, indicating that solvation of these salts was not as favorable in aqueous solution as for the lithium salts.

TABLE 2

Solubility and Heat of Solution Data

| Salt | Measured Solubility in Lysis/Binding | Reported Solubility in Water* | Measured Solubility in Wash I | Reported Solubility in Alcohol(s) | Heat of Aqueous Solution (kcal/mole) | Type of Heat |
|---|---|---|---|---|---|---|
| LiCl | at least 4 M | 18 M | at least 5 M | soluble in alcohol | −8.85 | exothermic |
| LiBr | at least 4 M | 19 M | at least 5 M | soluble in alcohol & ethanol | −11.67 | exothermic |
| CsCl | at least 4 M | 11 M | 2.5 M | very soluble in alcohol | +4.25 | endothermic |
| NH4Cl | 3 M | 7 M | 2.0 M | insoluble ethanol | +3.53 | endothermic |
| NaCl | at least 4 M | 6 M | 1.5 M | slightly sol in alcohol | +0.93 | endothermic |

TABLE 2-continued

Solubility and Heat of Solution Data

| Salt | Measured Solubility in Lysis/Binding | Reported Solubility in Water* | Measured Solubility in Wash I | Reported Solubility in Alcohol(s) | Heat of Aqueous Solution (kcal/mole) | Type of Heat |
|---|---|---|---|---|---|---|
| KCl | less than 3 M | 3 M | less than 1 M | slightly sol in alcohol, soluble in ethanol | +4.12 | endothermic |

*Note:
Data extrapolated to 20° C. from tabulated data in Handbook of Chemistry and Physics.

EXAMPLE 3

Evaluation of Detergents for RNA Purification

Much time and effort was spent screening detergents that would adequately lyse cells and also stay soluble in the Lysing/Binding Solution of the present invention. The Tween, Triton, Tergitol, Nonidet and Igepal family of detergents were examined along with a number of non-ionic detergent-like compounds.

It was discovered that many of these detergent formulations, when mixed with the other ingredients of the Lysing/Binding Solution, saponified or degraded over time and fell out of solution. For example, 10% Tween-20 (polyoxylene sorbitan monolaurate) did this. Similar performance was found using an equal mixture of Triton X-100 (t-octylphenoxy polyethoxyethanol) and Tween-20, though this mixture was stable for longer periods of time. This mixture, however, eventually saponified and separated. DGME (Diethyleneglycolmonoethylether) was chosen for testing, as it performs well, is highly soluble, stays in solution and is not as cost prohibitive as other Tween-20 substitutes. A mixture of Triton-X at 5% and DGME at 5% was found to work particularly well.

EXAMPLE 4

Evaluation of RNA Quality Using Bioanalyzer

To assess the quality of RNA purified using the reagents and methods of the present invention, RNA samples were analyzed using an Agilent 2100 Bioanalyzer (Agilent Technologies, Palo Alto, Calif.). This system may be used to assess the size and quality of the major ribosomal RNA bands by generating an electropherogram and by calculating the ratio between the 28 s and 18 s peak areas. Generally, two resolvable peaks with ratios greater than 1.5 indicate that the RNA sample is undegraded.

Figure 1:
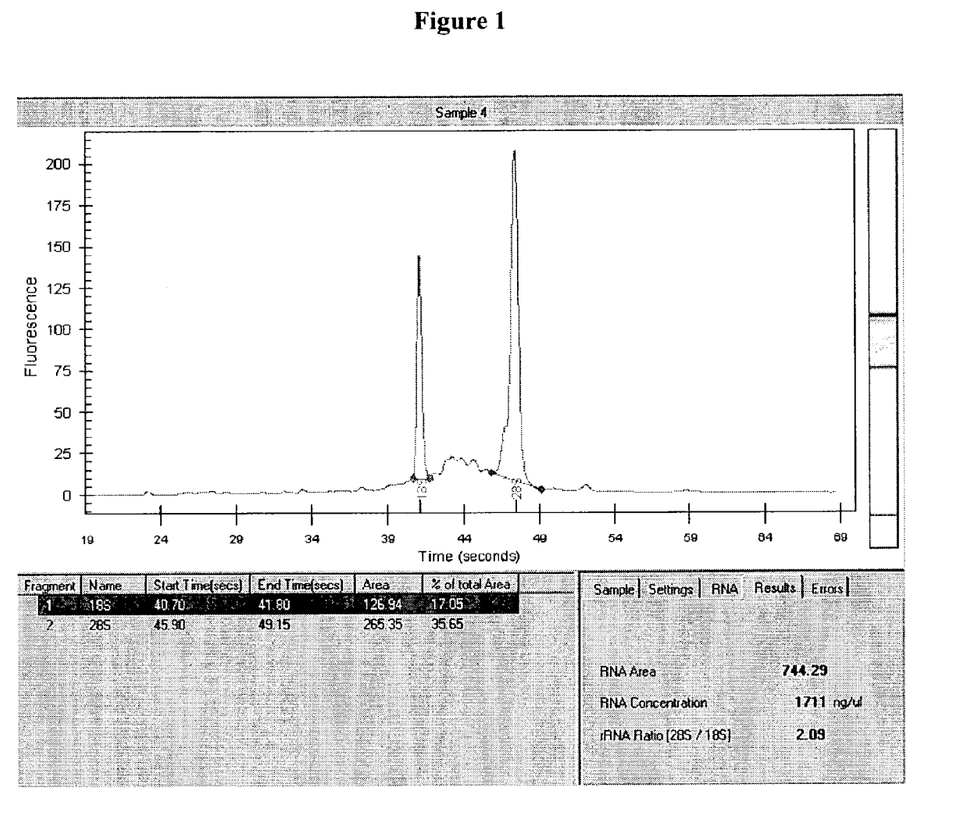
FIG. 1 depicts an electropherogram of Rat Spleen RNA purified according to the protocols described in Example 6.

RNA from a total of 40 mg Rat Spleen was purified according to the protocols described in Example 6, with the exception that the lysis was allowed to incubate at room temperature for an hour to enhance detection of any possible endogenous RNase activity. Following purification, 1 µl of each RNA sample was loaded into a well of an RNA LabChip® (Agilent Technologies, Palo Alto, Calif.) prepared in a reagent supplied by the manufacturer and according to the manufacturer's instructions. Following electrophoresis, the resulting electropherogram was examined (See, e.g., FIG. 1). All samples showed two distinct 28 s and 18 s peaks. The average 28 s to 18 s ratio was 2.03, with a range of 1.98 to 2.09 for all samples. The ratios were thus all greater than 1.5, indicating that the method of the present invention generated substantially undegraded RNA.

EXAMPLE 5

Isolation of RNA from Eukaryotic Cells

Eukaryotic AG cells were lysed in 200 µL of Binding/Lysing solution (4 LiCl, 5% Triton X-100, 5% DGME (diethylene glycol monoethyl ether), 10 mM EDTA, 1% sodium tungstate, in 100 mM TRIZMA at pH 8.8) for each sample up to 10 million cells, and in 400 µL Lysing/Binding Solution for 20 to 50 million cells. The cells were vortexed for 2 minutes at high speed, and then pipetted up and down 50 times, and vortexed again for another 2 minutes, in order to achieve complete homogenization and lysing. After homogenization, 200 µL or 400 µL of homogenized lysate was pipetted onto each purification column, depending upon the number of cells being added to the column. The purification column contained a borosilicate glass fiber membrane (Whatman D glass fiber membrane) within a basket and placed inside a 2 mL microfuge tube. The microfuge tube was then spun at maximum speed in a microcentrifuge for 1 minute. After centrifugation of lysate, the baskets for samples that contained 400 µL of lysate were transferred to a new tube, in order to continue with the Wash I Solution.

After centrifugation of lysate and subsequent binding of RNA to the borosilicate membrane surface, 200 µL or 400 µL of Wash I Solution (5 M LiCl and 55% ethanol), the same volume as the volume of lysate initially applied to the column, was added to the column material and spun at maximum speed in a microcentrifuge for 1 minute. The basket containing the membrane was then transferred to a new microfuge tube and 200 µL of Wash II Solution (5 mM EDTA, 70% ethanol, in 100 mM Tris HCl at pH 7.6) was added to the column material and spun at maximum speed in a microcentrifuge for 1 minute. The Wash II Solution addition and centrifugation steps were repeated once.

To elute the RNA from the solid support, the basket containing the membrane was transferred to a new microfuge tube and 50 µL of DEPC-treated water was added to the column material and spun at maximum speed for 1 minute.

Table 3 represents the data obtained using the described method for the various cell numbers tested. These results were compared to results obtained using another solid phase RNA method using the manufacturer's recommended instructions (Qiagen RNeasy Mini kit). Up to 10 million cells were tested using this alternative method, as recommended with the RNeasy Mini kit. The data obtained using the method and solutions of the present invention additionally represent data collected for 20 to 50 million cells, using the same size purification columns as for the smaller cell numbers, which were at 10 million or less. The data include yields calculated from the absorbance values at 260 nm (corrected by the absorbance at 320 nm), to which absorption from DNA contributed no more than 5% (as determined visually on agarose gels). The $A_{260}/A_{280}$ ratios were calculated according to the equation $(A_{260}-A_{320})/(A_{280}-A_{320})$. RNA samples proved to be stable, as initially examined on the Agilent 2100 Bioanalyzer. They were also stable as determined by heating the RNA-containing samples in a heat block at 37° C. for 1 hour, and subjecting the samples to electrophoresis in an agarose gel. Ribosomal RNA banding was present in all samples. Clean, stable and competitive quantities of RNA were obtained from all cell number samples examined in this experimental work.

TABLE 3

Isolation of RNA from Eukaryotic Cells Samples

| Number Cells (millions) | Solid Phase Kit | $A_{260}/A_{280}$ | Yield μg RNA per million cells | Total Yield μg RNA |
|---|---|---|---|---|
| 0.05 | Gentra | | | |
| | Mean | 1.93 | 7.7 | 0.38 |
| | sd | 0.09 | 0.89 | 0.04 |
| | Qiagen | | | |
| | Mean | 2.17 | 11.2 | 0.56 |
| | sd | 0.24 | 0.00 | 0.00 |
| 0.10 | Gentra | | | |
| | Mean | 2.08 | 11.5 | 1.15 |
| | sd | 0.14 | 0.38 | 0.038 |
| | Qiagen | | | |
| | Mean | 1.94 | 6.2 | 0.62 |
| | sd | 0.09 | 0.28 | 0.03 |
| 1 | Gentra | | | |
| | Mean | 2.01 | 10.25 | 10.25 |
| | sd | 0.02 | 0.34 | 0.34 |
| | Qiagen | | | |
| | Mean | 1.86 | 5.36 | 5.36 |
| | sd | 0.00 | 0.11 | 0.11 |
| 5 | Gentra | | | |
| | Mean | 2.03 | 9.11 | 45.5 |
| | sd | 0.02 | 0.72 | 3.6 |
| | Qiagen | | | |
| | Mean | 1.89 | 4.76 | 23.8 |
| | sd | 0.00 | 0.01 | 0.03 |
| 10 | Gentra | | | |
| | Mean | 2.24 | 12.39 | 123.9 |
| | sd | 0.02 | 1.47 | 14.66 |
| | Qiagen | | | |
| | Mean | 2.44 | 9.16 | 91.6 |
| | sd | 0.02 | 0.06 | 0.57 |
| 20 | Gentra | | | |
| | mn | 2.25 | 4.18 | 83.6 |
| | sd | 0.04 | 0.38 | 7.65 |
| 30 | Gentra | | | |
| | Mean | 2.23 | 3.32 | 99.8 |
| | sd | 0.04 | 0.07 | 2.03 |
| 40 | Gentra | | | |
| | Mean | 2.22 | 2.93 | 117.3 |
| | sd | 0.04 | 0.74 | 29.65 |
| 50 | Gentra | | | |
| | Mean | 2.18 | 1.91 | 107.5 |
| | sd | 0.05 | 1.12 | 17.69 |

EXAMPLE 6

Isolation of RNA from Various Mammalian Tissue Samples

Various rat and pig tissues were purified using the following tissue homogenization and purification protocol. Initially, 200 μL of Lysing/Binding Solution (4 LiCl, 5% Triton X-100, 5% DGME (diethylene glycol monoethyl ether), 10 mM EDTA, 10 mM TCEP, 1% sodium tungstate, in 100 mM TRIZMA at pH 8.8) was added for each 30 mg of tissue sample in a tube. A roto-stator was used to homogenize each sample on low speed until no visible chunks were detected, after which the roto-stator speed was increased to complete homogenization for an additional minute. After homogenization, 200 μL of homogenized lysate was added to a pre-clear column (Gentra). The pre-clear column cleared unwanted particulates from the tissue lysates, which would otherwise plug the borosilicate glass fiber purification column material if applied directly. Depending upon the tissue and extent of homogenization, the pre-clear column trapped particulates, while still allowing for the bulk of the applied lysis volume containing the RNA to wash through the filter. The pre-clear column was spun an additional minute to recover more volume from the trapped particulate materials, if deemed necessary.

After centrifugation in the pre-clear column, the cleared lysate at the bottom of the pre-clear tube was vortexed briefly. Then, the entire volume of cleared lysate (~200 μL) was pipetted onto the purification column, which contained a borosilicate glass fiber membrane (Whatman D glass fiber membrane) within a basket and placed inside a 2 mL microfuge tube. The microfuge tube was then spun at maximum speed in a microcentrifuge for 1 minute. The microfuge tube was then turned 180° in the microcentrifuge and centrifuged for an additional 2 minutes.

After centrifugation of lysate and subsequent binding of RNA to the borosilicate membrane surface, 200 μL of Wash I Solution (5 M LiCl and 55% ethanol) was added to the column material and spun at maximum speed in a microcentrifuge for 1 minute. The basket containing the membrane was then transferred to a new microfuge tube and 200 μL of Wash II Solution (5 mM EDTA, 70% ethanol, in 100 mM Tris HCl at pH 7.6) was added to the column material and spun at maximum speed in a microcentrifuge for 1 minute. The Wash II Solution addition and centrifugation steps were repeated once.

To elute the RNA from the solid support, the basket containing the membrane was transferred to a new microfuge tube and 50 µL of DEPC-treated water was added to the column material and spun at maximum speed for 1 minute.

Table 4 represents the data obtained using the described method and data obtained using another solid phase RNA method following the manufacturer's recommended instructions (Qiagen RNeasy Mini kit). The following tissues were tested: pig liver, pig spleen, pig lung, pig heart, rat spleen, rat brain, and rat ovaries. The data includes yields calculated from the absorbance values at 260 nm (corrected by the absorbance at 320 nm), to which absorption from DNA contributed no more than 5% (as determined visually on agarose gels). The $A_{260}/A_{280}$ ratios were calculated according to the equation $(A_{260} - A_{320})/(A_{280} - A_{320})$. RNA samples proved to be stable, as initially examined on the Agilent 2100 Bioanalyzer. They were also stable as determined by heating the RNA-containing samples in a heat block at 37° C. for 1 hour followed by subjecting the samples to electrophoresis in an agarose gel. Ribosomal RNA banding was present in all cases after heating.

Proteinase K (7 U/200 µL) was added to the Lysing/Binding Solution for pig heart tissue, and incubated for 10 minutes at 55° C. in order to examine whether this enzyme would improve RNA yields from cardiac muscle tissue. The results indicated that the Lysing/Binding Solution and Wash I Solution are sufficient at homogenizing and lysing the tissue samples, and at eliminating RNase activity from the tissue samples, without the use of proteinase K. Clean, stable and competitive quantities of RNA were obtained from all tissue samples examined in this experimental work showing that the methods and solutions of the present invention provide faster, less expensive, but effective methods for purifying RNA.

TABLE 4

Isolation of RNA from Mammalian Tissue Samples

| Tissue Sample Type | Solid Phase Kit | | $A_{260}/A_{280}$ | Yield µg RNA per mg Tissue | Total Yield µg RNA (30 mg Tissue) |
|---|---|---|---|---|---|
| Pig Liver | Gentra | | | | |
| | | Mean | 2.04 | 2.72 | 81.5 |
| | | sd | 0.01 | 0.78 | 23.5 |
| | Qiagen | | | | |
| | | Mean | 2.08 | 2.19 | 65.7 |
| | | sd | 0.00 | 0.25 | 7.6 |
| Pig Spleen | Gentra | | | | |
| | | Mean | 2.02 | 1.86 | 55.8 |
| | | sd | 0.01 | 0.42 | 12.5 |
| | Qiagen | | | | |
| | | Mean | 2.06 | 1.54 | 46.0 |
| | | sd | 0.02 | 0.26 | 7.8 |
| Pig Lung | Gentra | | | | |
| | | Mean | 2.01 | 0.71 | 21.3 |
| | | sd | 0.01 | 0.08 | 2.3 |
| | Qiagen | | | | |
| | | Mean | 2.04 | 0.16 | 5.0 |
| | | sd | 0.01 | 0.01 | 0.2 |
| Rat Spleen | Gentra | | | | |
| | | Mean | 1.94 | 5.21 | 156.3 |
| | | sd | 0.01 | 0.38 | 11.4 |
| | Qiagen | | | | |
| | | Mean | 1.96 | 2.76 | 83.0 |
| | | sd | 0.02 | 0.32 | 9.5 |
| Rat Ovaries | Gentra | | | | |
| | | Mean | 2.08 | 1.50 | 45.1 |
| | | sd | 0.01 | 0.18 | 5.5 |
| | Qiagen | | | | |
| | | Mean | 2.08 | 1.20 | 36.0 |
| | | sd | 0.01 | 0.23 | 6.8 |
| Rat Brain | Gentra | | | | |
| | | Mean | 2.01 | 0.76 | 22.9 |
| | | sd | 0.01 | 0.04 | 1.3 |
| | Qiagen | | | | |
| | | Mean | 2.06 | 0.59 | 17.7 |
| | | sd | 0.01 | 0.06 | 1.7 |
| Pig Heart (without ProK) | Gentra | | | | |
| | | Mean | 2.18 | 0.22 | 6.7 |
| | | sd | 0.08 | 0.03 | 0.8 |
| | Qiagen | | | | |
| | | Mean | 2.45 | 0.02 | 0.8 |
| | | sd | 0.07 | 0.01 | 0.2 |
| Pig Heart (With ProK) | Gentra | | | | |
| | | Mean | 2.02 | 0.25 | 7.6 |
| | | sd | 0.07 | 0.04 | 1.3 |
| | Qiagen | | | | |
| | | Mean | — | 0.01 | 0.3 |
| | | sd | — | 0.00 | 0.0 |

EXAMPLE 7

RNA Solid Phase Purification Performance Using Different Chloride Salts and Compared to LiCl and LiBr Salts Spleen tissue was purified using the tissue homogenization and purification protocol (described in Example 6 above), using a Lysing/Binding Solution made with the cesium, ammonium and sodium chloride salt concentrations described in Example 2, but by keeping the remaining solution constant at 5% Triton X-100, 5% DGME (diethylene glycol monoethyl ether), 10 mM EDTA, 10 mM TCEP, 1% sodium tungstate, in 100 mM TRIZMA at pH 8.8. In addition, a Lysing/Binding Solution containing 5 M lithium chloride and bromide were also added for comparison. For each 40 mg of spleen tissue added to each experimental solution lysate, 200 µL of Lysis/Binding Solution was added to the sample in a tube for homogenization. Subsequent additions of 200 µL of homogenized lysate were added to the pre-clear and purification columns, using homogenization and purification protocols as described for tissue in Example 6. In the groups in which the Lysing/Binding buffer was varied, a Wash I Solution containing 5 M lithium chloride in 55% ethanol was used for all groups, and the remaining Wash 2 and Elution Solution contained the same components as those described in Example 6.

In addition to the groups described above, in which the salts were varied in the Lysing/Binding Solution, another set of groups were purified. This other set of groups were purified where the Lysing/Binding Solution was kept constant as described above, 4 M lithium chloride was used as the salt in the Lysing/Binding Solution, and the Wash I Solution was made with the maximum solubilized salt quantities for the cesium, ammonium and sodium chloride salts (as described in Example 2), in 55% ethanol. In addition, a Wash I containing 5 M lithium bromide was also added for comparison. All other solutions contained the same components as those described in Example 6.

Table 5 represents the data obtained for the groups using the different chloride salts in the Lysing/Binding Solution, and for the groups using the different chloride salts in the Wash I Solution. The data include yields calculated from the absorbance values at 260 nm (corrected by the absorbance at 320 nm). No more than 5% of the nucleic acid present was DNA (as determined visually on agarose gels) for all the groups in which the Wash I Solution was varied and for the lithium chloride and bromide groups. The agarose gels showed that a significant portion of the absorbance detected at 260 nm was due to DNA for those Lysing/Binding Solution prepared with the cesium, ammonium and sodium chloride salts. DNA contamination was no more than 5% in the lithium chloride and bromide Lysing/Binding Solution groups (as determined visually on agarose gels). The $A_{260}/A_{280}$ ratios were calculated according to the equation $(A_{260}-A_{320})/(A_{280}-A_{320})$. RNA samples proved to be stable, as initially examined on the Agilent 2100 Bioanalyzer. They were also stable as determined by heating the RNA-containing samples in a heat block at 37° C. for 1 hour, followed by subjecting the samples to electrophoresis in an agarose gel. Ribosomal RNA banding was present in all cases after heating in this experiment. In previous work in 2.5 M LiCl Wash I Solutions, however, RNase activity was detected at least half of the time, as degraded RNA in the final eluted RNA product. That experimental work demonstrated that at least 5 M LiCl was needed in the Wash I Solution. It is likely that RNase activity would be detected using the other chloride salts as well, since their solubility in ethanol is limited at least some proportion of the time (and depending upon the tissue from which the RNA is purified).

In all cases where another salt was substituted in for lithium chloride or lithium bromide in either the Lysing/Binding Solution or the Wash I Solution, the RNA yields were substantially less than for those in which the lithium salts were used. The lysates composed of the cesium, ammonium and sodium salts were gelatinous in nature. It is suspected that homogenization and lysing are not as complete for these salts, as compared to when the lithium salts are used, resulting in more gelled particulates and lower RNA yields.

TABLE 5

RNA Purification Yield Using Various Chloride Salts

| Lysing/Binding Salt | Lysing/Binding Salt Concentration | Wash I Salt | Wash 1 Salt Concentration | A260/A280 | Total Yield µg RNA (40 mg Tissue) |
|---|---|---|---|---|---|
| LiCl | 4 M | LiCl | 5 M | | |
| Mean | | | | 1.95 | 52.53 |
| sd | | | | 0.02 | 8.79 |
| LiCl | 4 M | NaCl | 1.5 M | | |
| Mean | | | | 1.98 | 33.37 |
| sd | | | | 0.02 | 20.65 |
| LiCl | 4 M | NH4Cl | 2 M | | |
| Mean | | | | 2.00 | 30.48 |
| sd | | | | 0.02 | 6.63 |
| LiCl | 4 M | CsCl | 2.5 M | | |
| Mean | | | | 2.01 | 25.32 |
| sd | | | | 0.01 | 4.44 |
| LiCl | 4 M | LiBr | 5 M | | |
| Mean | | | | 2.01 | 39.41 |
| sd | | | | 0.02 | 6.59 |
| NaCl | 4 M | LiCl | 5 M | | |
| Mean | | | | 1.91 | 9.64 |
| sd | | | | 0.01 | 3.17 |
| NH4Cl | 3 M | LiCl | 5 M | | |
| Mean | | | | 1.97 | 15.43 |
| sd | | | | 0.06 | 1.70 |
| CsCl | 4 M | LiCl | 5 M | | |
| Mean | | | | 1.87 | 9.18 |
| sd | | | | 0.01 | 1.41 |
| LiBr | 4 M | LiCl | 5 M | | |
| Mean | | | | 1.96 | 51.65 |
| sd | | | | 0.02 | 16.94 |

EXAMPLE 8

Use of Purified RNA for Microarray Analysis

Isolation of RNA from K562 cell line: 50 million frozen cell pellets were resuspended in 1 ml Lysis/Binding Solution (4 M LiCl, 10% Triton X-100, 5% DGME, 10 mM EDTA, 10 mM TCEP, 1% sodium tungstate, in 100 mM TRIZMA at pH 8.8). Cells were lysed and total RNA was purified as per Solid Phase RNA Cell protocol (see Example 5).

Post-purification, RNA samples were visualized on an Agilent 2100 Bioanalyzer chip, heated to 37° for one hour, and subsequently visualized on a 1% Agarose gel to ensure that the RNA was stable and of good quality. RNA was then quantified with the Beckman DU-64 spectrophotometer.

Reverse Transcription and cDNA Labeling: cDNA was reversed transcribed from the purified RNA template using an oligo dT primer and amino allyl-modified dUTP according to the Amersham Biosciences CyScribe Post-Labeling Kit protocol. The oligo dT primed cDNA was then purified with the CyScribe GFX Purification Kit and labeled with Cy3 as per the Amersham protocol. Cy3-labeled cDNA was then purified as per the GFX protocol and lyophilized in the speed vac for 25 minutes.

Hybridization and Scanning: Test slides from Genomic Solutions were washed and dried as per the manufacturer's protocol. The dried Cy3-cDNA pellet was resuspended in 5 µl of nanopure water. 25 µl Genomic Solutions 1× Hybridization Solution was added to resuspended pellet, and sample was heated to 95° C. for 2 minutes. The sample was then applied to slide underneath a lifter slip. The slide and slip were sealed in the hybridization chamber, wrapped in aluminum foil and incubated in a 55° C. water bath overnight. Post-hybridization, the slide was washed as per the Genomic Solutions hybridization protocol with buffers containing increasing amounts of salts to increase the stringency of the wash process. Slides were dried and stored in a dark container until scanning was complete. Slides were scanned with the Scan Array 5000 using the Scan Array Express option.

Microarray Results: Total RNA purified with the present Solid Phase RNA Purification system was successfully displayed using microarray technology as visualized as a pattern of discreet and quantifiable circles present on slides hybridized with our Cy3 labeled cDNA probe.

All publications, patents and patent documents are incorporated by reference herein, as though individually incorporated by reference. The invention has been described with reference to various specific and specific embodiments and techniques. However, it should be understood that many variations and modifications may be made while remaining within the scope of the invention.

We claim:

1. A formulation for isolating and purifying nucleic acids comprising:
   a lithium salt at a concentration of about 4–10 M, a detergent, and a buffer, wherein the formulation has a pH above about 7 and lacks a chaotrope.
2. The formulation of claim 1, further comprising a chelating agent.
3. The formulation of claim 1, further comprising a reducing agent.
4. The formulation of claim 1, wherein the lithium salt is lithium chloride.
5. The formulation of claim 1, wherein the solution has a pH between about 7 and about 9.
6. The formulation of claim 1, wherein the detergent is an anionic, cationic, zwitterionic or non-ionic detergent.
7. The formulation of claim 6, wherein the detergent is a non-ionic detergent.
8. The formulation of claim 7, wherein the detergent is a tween, triton, nonidet, igepal or tergitol.
9. The formulation of claim 1, wherein the detergent is a mixture of triton-x and diethyl glycol monoethyl ether (DGME).
10. The formulation of claim 1, wherein the detergent is a mixture of 5% v/v triton-x and 5% v/v DGME.
11. The formulation of claim 1, wherein the detergent is present at a concentration of about 10% v/v of the final volume of the solution.
12. The formulation of claim 1, wherein the buffer has a pKa of at least about 8.
13. The formulation of claim 1, wherein the chelating agent is EDTA.
14. The formulation of claim 1, wherein the reducing agent is Tris (carboxyethyl) phosphine (TCEP).
15. The formulation of claim 1, further comprising a tungstate.
16. An article of manufacture for isolating and purifying nucleic acids comprising:
   the formulation of claim 1; and
   a solid support.
17. The formulation of claim 1, further comprising a surfactant.
18. The formulation of claim 17, wherein the surfactant is DGME.
19. A formulation for isolating and purifying nucleic acids comprising:
   a lithium salt at a concentration of about 4–10 M, a detergent, and a buffer, wherein the formulation has a pH below about 4.5 and lacks a chaotrope.
20. An article of manufacture for isolating and purifying nucleic acids, comprising:
   the formulation of claim 19; and
   a solid support.

* * * * *